| United States Patent [19] | [11] 4,278,563 |
|---|---|
| Fremont et al. | [45] Jul. 14, 1981 |

[54] COPPER CHLORIDE CONTAINING CATALYSTS FOR THE PREPARATION OF FURAN COMPOUNDS

[75] Inventors: Joseph M. Fremont, Glen Mills, Pa.; Donald I. Garnett, Hockessin, Del.

[73] Assignee: E. I. Du Pont de Nemours and Company, Wilmington, Del.

[21] Appl. No.: 109,263

[22] Filed: Jan. 18, 1980

Related U.S. Application Data

[63] Continuation-in-part of Ser. No. 29,101, Apr. 10, 1979, abandoned.

[51] Int. Cl.$^3$ .................. B01J 27/10; B01J 27/08; C07D 307/36
[52] U.S. Cl. .................. 252/441; 260/346.11
[58] Field of Search .................. 252/441

[56] References Cited

U.S. PATENT DOCUMENTS

| 3,403,108 | 9/1968 | Leftin et al. ............ 252/441 |
| 3,993,593 | 11/1976 | Kameko et al. ............ 252/441 |
| 4,155,879 | 5/1979 | Mimoun et al. ............ 252/441 |
| 4,172,838 | 10/1979 | Garnett et al. ............ 260/346.11 |

FOREIGN PATENT DOCUMENTS

| 2264462 | 10/1973 | Fed. Rep. of Germany ...... 252/441 |
| 52-77049 | 6/1977 | Japan. |
| 265119 | 6/1970 | U.S.S.R. |

*Primary Examiner*—P. E. Konopka

[57] ABSTRACT

A process for preparing a furan compound by contacting a diolefin such as butadiene with a catalyst at a low pressure and a low temperature is provided. In this process, a diolefin, an oxygen-containing gas and water containing HCl are contacted with a catalyst which is a support having deposited thereon copper chloride, an alkali metal chloride and at least one of palladium chloride and iodide, usually cuprous iodide. Temperature of the reaction is usually in the range of about 80°–125° C. and the pressure is usually in the range of about 1–5 atmospheres. Cyclic operation between furan production and catalyst oxidation is also provided.

6 Claims, No Drawings

COPPER CHLORIDE CONTAINING CATALYSTS FOR THE PREPARATION OF FURAN COMPOUNDS

CROSS-REFERENCE TO RELATED APPLICATION

This application is a continuation-in-part of application Ser. No. 29,101, filed Apr. 10, 1979, now abandoned.

DESCRIPTION

1. Technical Field

This invention relates to processes for the preparation of furan compounds, and more particularly to processes for the preparation of furan compounds from diolefins, particularly butadiene.

2. Background Art

Furan is a chemical useful in furan resins and, more importantly, as a raw material for the manufacture of tetrahydrofuran. However, furan today is prepared from natural pentose contained in corn or oat hulls through furfural as an intermediate. To reduce the cost of tetrahydrofuran, it is produced today from acetylene and formaldehyde through 1,4-butynediol and 1,4-butanediol as intermediates. While this is a satisfactory process, it is moderately complex in the number of steps required to reach tetrahydrofuran as the final product. More importantly, however, acetylene is becoming more expensive due to energy inefficiencies involved in its manufacture.

There have been attempts over the years to produce furan directly by the catalystic oxidation of butadiene. These attempts have generally been under harsh processing conditions, e.g., at temperatures higher than about 375° C., which result in overoxidation to carbon oxides and furan decomposition. Such high temperature, vapor phase processes are exemplified by U.S. Pat. Nos. 3,238,225; 3,716,545; 3,775,508; 3,864,279; 3,906,009; 3,912,763; 3,928,289 and 4,026,820.

A process for preparing furan by oxidation of butadiene with molecular oxygen at lower temperatures (40°–150° C. either in a vapor phase reaction or a liquid phase reaction is described in Japanese Patent Application Publication No. 52-77049 dated June 29, 1977. In one aspect of the process described therein, a palladium salt and a thallium or indium salt are dissolved in acidified water and then butadiene and oxygen are passed through the solution. A similar process is described in Russian Patent No. 265119 dated June 24, 1970. In this process, butadiene (or butadiene and air) is passed through an acidic, aqueous solution of cupric chloride and palladium chloride at a temperature of 60°–110° C. Cuprous chloride can be used in place of palladium chloride. Both of these processes suffer deficiencies of impractical rates of reaction and excessively low reaction life.

DETAILED DESCRIPTION

According to the present invention, there is provided a process for preparing a furan compound, which process comprises contacting a catalyst consisting essentially of a support having deposited thereon (1) copper chloride,
(2) an alkali metal chloride, and
(3) at least one of palladium chloride and an iodide, in a reaction zone with (4) a molecular oxygen-containing gas,
(5) a diolefin of the formula

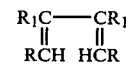

where
each R is H or an alkyl group of 1–4 carbon atoms, and
each $R_1$ is H, a halide or an alkyl group of 1–4 carbon atoms, and (6) water vapor containing about 0.5–5% by weight of HCl.

In one embodiment of the present invention there is provided a process for preparing furan comprising: contacting a gaseous stream comprising (1) air, (2) butadiene, and (3) water vapor containing about 0.5–5% by weight HCl based on the weight of the water, in a reaction zone maintained at a temperature in the range of about 80°–125° C. and at a pressure in the range of about 1–5 atmospheres, with a catalyst consisting essentially of a silica, alumina or silica-alumina support having deposited thereon (1) about 0.5–30%, by weight of the support, of copper chloride, (2) about 0.1–2%, by weight of the support, of cuprous iodide or about 0.01–2%, by weight of the support, of palladium chloride, and (3) 5–7%, by weight of the support, of calcium chloride.

The present invention is a vapor phase process for the preparation of a furan compound, such as furan, from a diolefin especially butadiene, using a catalyst system consisting essentially of copper chloride, preferably a mixture of cuprous and cupric ions; an alkali metal chloride, preferably calcium chloride, and at least one of an iodide, preferably cuprous iodide, and palladium chloride, deposited on an inert support. This process, which can be conducted at low temperatures and pressures, produces the furan compound at good conversions and yields and at practical rates of reaction.

A 1,3-diolefin is used as the starting material in the present process. The useful 1,3-diolefins have the formula

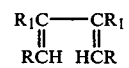

where
each R is H or an alkyl group of 1–4 carbon atoms (preferably methyl), and
each $R_1$ is H, an alkyl group of 1–4 carbon atoms (preferably methyl) or a halide such as chloro or iodo (preferably chloro),
with the proviso that the total number of carbon atoms does not exceed 8, preferably does not exceed 5.

Illustrative diolefins are 1,3-butadiene; 1,3-pentadiene; 2-chloro-1,3-butadiene; 2-methyl-1,3-butadiene; 2-iodo-1,3-butadiene; 1,3-hexadiene, 2,4-hexadiene; 2,3-dimethyl-1,3-butadiene; 3,4-dimethyl-2,4-hexadiene; 4,6-octadiene; and 1,3-octadiene. Of these diolefins, the first four listed are preferred due to commercial availability, with 1,3-butadiene being most preferred. Mixtures of diolefins can be used if desired.

When used in the process of the invention, the diolefin can be fed separately and undiluted, mixed with a gas inert to the reaction, such as nitrogen, carbon monoxide or carbon dioxide, or mixed with an oxygen-containing gas such as air. In a preferred embodiment of the invention, the diolefin is mixed with the oxygen-containing gas and water vapor containing about 0.5–5% by weight HCl to form a gaseous stream which is then contacted with the catalyst. However, cyclic addition of the gases to a reactor can be employed. While there does not appear to be anything critical about the gaseous stream's compositional make-up, having about 10–50% by volume of water vapor in the gaseous feed has been found useful. The stream contains about 1–50% by volume of butadiene with the balance being air. A preferred HCl content is about 1–2% by weight, based on the weight of water, when palladium is used in the catalyst and about 3–5% by weight, based on the weight of water, when an iodide is used in the catalyst.

The oxygen-containing gas employed can be molecular oxygen as such or molecular oxygen used with a diluent inert to the reaction such as nitrogen or the like. Typical molecular oxygen-containing gases are air, which is preferred, flue gases or synthesis gases which contain residual oxygen, and any source of molecular oxygen free of contaminants detrimental to the desired reaction.

The catalyst used in the present invention consists essentially of an inert support, preferably of silica, alumina, silica-alumina or mixtures of these, in the form of pellets, powders or other configurations appropriate for use in a fixed, moving or fluid bed reactor. Illustrative other supports are titania, zirconia and other ceramics well known to those skilled in the art. Deposited on the support is copper chloride, preferably as a mixture of cuprous chloride and cupric chloride, an alkali metal chloride, and at least one of palladium chloride and an iodide compound, typically cuprous iodide. When iodide is deposited on the support, it is usually as cuprous iodide even though iodide is fed to the reaction system as hydrogen iodide or as an alkali metal iodide.

The alkali metal chloride used can be a divalent one such as calcium chloride, magnesium chloride, strontium chloride or barium chloride, or it can be a monovalent one such as sodium chloride, potassium chloride or lithium chloride. Divalent chlorides are preferred for their effectiveness, and calcium chloride is most preferred.

The copper chloride is usually present on the support at a concentration in the range of about 0.5–30%, preferably 8–12%, by weight of the support. The alkali metal chloride is present at a concentration of 0.5–10%, preferably 5–7%, by weight of the support. Palladium chloride, when it is used, is present at a concentration of 0.01–2%, preferably 0.02–0.06%, by weight of the support. Iodide is ordinarily present at a concentration of 0.1–2%, preferably 0.03–0.05%, by weight of the support.

The catalyst used in the process of the invention is conveniently prepared by dissolving at least one of cupric chloride and cuprous chloride, an alkali metal chloride and palladium chloride (when it is used) in a dilute HCl solution. One volume of solution so obtained is added to 2 volumes of catalyst support which absorbs essentially all the added solution. The material is then oven dried, usually under vacuum at 90°–100° C. In the event iodide addition is desired, a second impregnation is made using the desired iodide concentration in aqueous solution. A second suitable method involves feeding HI solution in the aqueous HCl feed to the catalyst vapor phase until the desired iodide has been charged.

The process of the invention can be carried out at a temperature in the range of about 80°–125° C., preferably about 100°–125° C. As would be expected, rates of furan production are reduced at the lower temperatures. Reaction pressures are typically in the range of about 1–5 atmospheres, preferably about atmospheric pressure. It is the diolefin's partial pressure in the gas stream contacted with the catalyst that determines the particular pressure used.

The diolefin flow rate through the catalyst contained in a reaction vessel does not appear to be critical. As will be apparent, the flow rate should not be so fast as to give inadequate contact time between the diolefin and the catalyst or so slow as to enable the resulting furan product time to decompose or polymerize. It is preferred that the catalyst be in a fixed bed as is known to those skilled in the art, and that the reaction off-gases containing furan product be removed from the reaction vessel promptly. The optimum contact time between the diolefin and catalyst depends on many factors and is readily determined by one skilled in the art.

Since the reaction system is very corrosive, the reactor for carrying out the process of the invention should be made of a material which is not corroded. Illustrative materials are glass or ceramic-lined metals, titanium, tantalum-clad metals, impregnated graphite tubes and the like.

Another embodiment of the invention is a two-step cyclic process wherein furan is produced in a first step by contacting the diolefin with the catalyst, and cuprous ion on the catalyst is oxidized to cupric ion in a second step by contacting the catalyst containing excess cuprous ion with the above-described oxygen-containing gas.

In a representative cyclic operation, a feed of butadiene and nitrogen is contacted with the catalyst until butadiene starts being detected in the off-gases. It is theorized that butadiene is absorbed by the catalyst and takes some intermediate compound form. The butadiene feed is turned off and air is introduced to the reactor and fed in until oxygen consumption drops, indicating that oxidation of the catalyst is essentially complete. The air is then turned off and butadiene again fed to the catalyst. Water with HCl is fed at all times. Such cyclic operation seems to give a higher concentration of furan in the off-gases for a longer period of time. When the furan yield then drops below some predetermined level, air is reintroduced for reoxidation of the catalyst. To maintain a high furan production rate, at least two reactors can be operated sequentially so that while the catalyst in one reactor is being oxidized, furan is being produced in the second reactor. An advantage of cyclic operation is that less palladium can be used in the catalyst. An alternative to cyclic operation is continuous circulation of the catalyst bed.

In the examples, concentrations were determined by gas chromatographic analyses. The samples were injected into a $10' \times 1/8''$ column of "Polopak N" for determination of their air, carbon dioxide, butadiene and furan contents. Analyses were carried out at 175° C. with helium carrier gas at 33 ml/min. The areas of the peaks in the chromatograph were converted to volume percents of components using factors determined by calibrations with known quantities of components. In all of the examples except Example 1, water was removed from the reaction off-gases by an air-cooled condenser prior to gas analysis.

The invention can be further understood by the following examples in which percentages are by volume unless otherwise stated.

EXAMPLE 1

To 100 g of a silica powder were added 50 cc of water having dissolved therein 0.5 g $PdCl_2$, 4 g $CuCl_2.2H_2O$, 2 g LiCl and 2 cc of concentrated HCl (aqueous solution of 36% by weight HCl). The resulting impregnated catalyst was dried overnight in an oven maintained at 130° C. A 0.95 cm × 12.7 cm (3/8"×5") stainless steel U-shaped tube reactor heated in a sand bath to a desired temperature was charged with 8.3 g of catalyst.

Gaseous reactants fed to the reactor were first mixed and then fed to one end of the tube reactor. At 125° C. and a feed rate of 73 cc/min with a feed composed of 45 cc of water vapor with 1% by weight HCl, 9 cc of butadiene, 11.7 cc of air and 7.3 cc of $N_2$, the composition of the gaseous product, by volume, analyzed at about 0.25% $CO_2$, 26.9% water, 31.2% butadiene, 0.5% furan, 0.1% oxygen and 41.1% $N_2$. Ninety-six minutes later the furan content in the gaseous product was about 0.26%. At 152 minutes, the furan content was about 0.28% and at 217 minutes it was about 0.24%. Butadiene in the feed was turned off and the catalyst was reoxidized by passing air through the reactor for 90 minutes. When the butadiene feed was restarted furan content in the gaseous product was 0.38% at 110° C.

EXAMPLE 2

A solution of 5 g $PdCl_2$, 5 g KCl, 50 g $CuCl_2.2H_2O$ and 15 cc of concentrated HCl in 200 cc water was added to 600 g of 1/8" alumina pellets (Houdry 100 S) and oven dried at 100° C. for about 12 hours under vacuum. The resulting catalyst was charged to a glass reactor oil-heated to 125° C.

Gaseous reactants (except water) were mixed in a manifold and fed to the reactor through a glass distributor located in the bottom of the reactor. The water-HCl feed was fed in a tube passing through the top of the reactor and the catalyst bed to preheat the water. At the bottom of the reactor, the water vaporized and mixed with the other gases discharged from the distributor. Gaseous feed of (1) 300 cc/min steam containing 1% by weight HCl, (2) 200 cc/min air, (3) 200 cc/min $N_2$ and (4) 25 cc/min butadiene were fed into the reactor and contacted with the catalyst. After 7 minutes, furan content in the gaseous product was 2%; after 97 minutes it was 2.6% and after 5 hours it was 1.8%. The run was terminated after 5 hours.

EXAMPLE 3 (Best Mode)

A catalyst was prepared as in Example 2 except the catalyst consisted of 50 g $CuCl_2.2H_2O$, 1 g $PdCl_2$, 33 g $CaCl_2$ and 5 g CuCl on 500 g of the alumina pellets.

After the catalyst was charged to the oil-heated glass reactor maintained at a temperature of 95°-100° C., the gas feeds were started at the following rates: 12 cc/min of butadiene, 200 cc/min of $N_2$, 125 cc/min of air and 250 cc/min of water vapor which contained 2% by weight of HCl. For a period of 6 hours, only a trace of furan was present in the off-gases. After this period of time, the butadiene and $N_2$ feeds were turned off and the air feed increased to 250 cc/min for a period of two hours. After this period, the air feed was turned off and the butadiene feed rate increased to 70 cc/min. After 20 minutes at the new feed rates, furan was analyzed in the off-gases at a concentration of 7.2%. Furan concentration in the off-gases after 80 minutes was 15% and then declined to 5% after 120 minutes.

We claim:

1. A catalyst consisting essentially of a support having deposited thereon
   (a) 0.5-30%, by weight of the support, of a mixture of cuprous chloride and cupric chloride,
   (b) 0.5-10%, by weight of the support, of an alkali metal chloride, and
   (c) at least one of
       (1) 0.01-2%, by weight of the support, of palladium chloride, and
       (2) 0.1-2%, by weight of the support, of an iodide compound.

2. The catalyst of claim 1 in which the component in (c) is palladium chloride.

3. The catalyst of claim 1 in which the component in (c) is cuprous iodide.

4. The catalyst of claim 1 in which the alkali metal chloride is of a divalent alkali metal.

5. The catalyst of claim 4 in which the alkali metal chloride is calcium chloride.

6. A catalyst consisting essentially of a support having deposited thereon
   (a) 0.5-30%, by weight of the support, of a mixture of cupric chloride and cuprous chloride,
   (b) 0.5-10%, by weight of the support, of calcium chloride,
   (c) 0.01-2%, by weight of the support, of palladium chloride.

* * * * *